United States Patent [19]

Dahneke

[11] 4,358,302

[45] Nov. 9, 1982

[54] APPARATUS FOR SEPARATION OF GAS BORNE PARTICLES

[75] Inventor: Barton E. Dahneke, Palmyra, N.Y.

[73] Assignee: The University of Rochester, Rochester, N.Y.

[21] Appl. No.: 209,613

[22] Filed: Nov. 24, 1980

[51] Int. Cl.³ ............................................. B01D 57/00
[52] U.S. Cl. ........................................ 55/392; 55/17; 55/270; 239/424; 250/288
[58] Field of Search ................... 73/863.21, 28; 55/17, 55/392, 270; 239/423, 424; 250/281, 288

[56] References Cited

U.S. PATENT DOCUMENTS

| | | | |
|---|---|---|---|
| 2,578,422 | 12/1951 | Guillot | 239/422 |
| 2,951,554 | 9/1960 | Becker | 55/17 |
| 3,465,500 | 9/1969 | Fenn | 55/17 |
| 3,583,663 | 6/1971 | Campargue et al. | 239/102 |
| 3,616,596 | 11/1971 | Campargue | 55/17 |
| 3,854,321 | 12/1974 | Dahneke | 73/28 |
| 3,944,399 | 3/1976 | Gspann | 55/392 |

FOREIGN PATENT DOCUMENTS

| | | | |
|---|---|---|---|
| 2805958 | 8/1979 | Fed. Rep. of Germany | 55/17 |
| 1041056 | 5/1953 | France | 239/422 |
| 534476 | 2/1942 | United Kingdom | 239/422 |

OTHER PUBLICATIONS

Nuclear Energy Maturity, Zaleski, Pergamon Press, (1975) Article, "On Aerodynamic Separation Methods", Camparague, et al.

Israel & Friedlander, J., Col. & Intf. Sc., 24, 3,330 (1967).

Dahneke & Cheng, J. Aero. Sc., 10, 257 (1979).

Primary Examiner—Bernard Nozick
Attorney, Agent, or Firm—Martin LuKacher

[57] ABSTRACT

Suspended particles which may be small solids or liquid particles or particles consisting of both solid and liquid components or relatively heavy molecules suspended in a lighter suspending gas are formed into a continuum source particle beam upon expansion of the suspension through a nozzle into a vacuum environment. The flow of the particle containing gas into the nozzle is confined by a flow of clean, particle free gas, as between a core and a sheath thereof, such that the particles have the same position at the inlet of the nozzle or at some location downstream of the inlet, such as the exit of the nozzle, thereby allowing only those particles containing the trajectory corresponding to the selected particle properties to be transmitted through one or more collimator holes or skimmers which are disposed a sufficient distance from the nozzle exit. The particle properties which determine their trajectory are particle mass and dimensions. The controlled flows into the nozzle enable the location, shape and dimensions of the collimator holes to be specified in accordance with the trajectory of the particles of selected mass and dimensions to be separated. Through the use of a plurality of collimators which define different angles, the resolution of particles which may be separated may be increased by defining double valued, narrow transmission functions.

13 Cla

APPARATUS FOR SEPARATION OF GAS BORNE PARTICLES

DESCRIPTION

The present invention relates to apparatus for the separation of suspended particles, which may be small particles of liquid or solid material, or a combination of both, mostly under a micron in diameter or heavy molecules suspended in a lighter gas, and particularly to the separation of particles through the use of a continuum source particle beam which is the stream of particles generated when a gaseous suspension of particles expands through a nozzle into a vacuum environment. The term "nozzle" as used herein should be taken to mean any device which provides a limiting orifice, such that the flow is naturally or constrained to be converging upstream of the limiting orifice.

The present invention is especially useful when the size and/or composition of gas borne particles, such as the molecular species contained in a gas mixture, is to be determined, as for the control of the chemical or other industrial processes or for the separation of particles, such as isotope species, or for the rapid introduction of suspended particles of selected properties into a high vacuum environment at known transmission efficiency.

Various techniques have been discussed in the literature for aerodynamically separating particles according to their size and mass. A survey of such techniques is found in the text "Nuclear Energy Maturity" edited by Pierre Zaleski and published by Pergamon Press (1975). The article is entitled "On Aerodynamicc Separation Methods" and is authored by Campargue, Anderson, Fenn, Hamel, Muntz and White. One of these aerodynamic separating devices involves entrainment of the gas to be separated in an expanding beam of the lighter suspending gas such that shock waves are produced which enable separation at a probe inlet. U.S. Pat. Nos. 3,465,500; 3,583,633 and 3,616,596, some of which are discussed in the above mentioned article, show some of these aerodynamic devices. The expansion of a gas containing suspended particles to form a continuum source beam is the subject of experiments described in an article by Israel and Friedlander which appeared in the Journal of Colloid and Interface Science, Volume 24, No. 3, page 330, July 1967. A device for generating a continuum source beam and analyzing the separated particles by time of flight measurement is shown in U.S. Pat. No. 3,854,321 issued to Barton E. Dahneke on Dec. 17, 1974. This patent also describes an aerodynamic separation apparatus. An understanding of continuum source beams which mathematically presents some of the theory of operation thereof has recently been presented in an article by Dahneke and Cheng which appeared in the Journal of Aerosol Science, Volume 10, page 257, May 1979.

An expansion of the analysis in the Dahneke and Cheng article has resulted in the discovery of improved designs for particle separation apparatus using continuum source particle beams in accordance with the present invention. More particularly, the resolution of apparatus for separating gas borne particles, that is the capability of such apparatus to isolate a selected particle size, is improved in accordance with the invention. Embodiments of the invention involving the use of one or a plurality of collimators presents the possibility of isolating particles, such as the isotopes of heavy molecules (e.g., the isotopes of uranium hexafluoride) which are close in molecular weight. Reference may be had to the following articles for further information respecting the discoveries and analysis upon which the present invention is based: Dahneke, "Sampling and Analysis of Suspended Particles and Vapors by Continuum Source Particle Beams" in the text "Emission Control from Stationary Power Sources: Technical, Economic and Environmental Assessments," Edited by A. J. Engel, S. M. Slater and J. W. Gentry, AIChE Symposium Series No. 201, Volume 76 Published by the American Institute of Chemical Engineers, New York, 1980; and Dahneke and Hoover, "Size Separation of Aerosol Beam Particles," Paper 169, 12th International Symposium on Rarefied Gas Dynamics, Charlottesville, Virginia, July 7-12, 1980.

Accordingly it is an object of the present invention to provide improved apparatus for the separation of gas borne particles.

It is a further object of the present invention to provide improved apparatus using continuum source particle beams generated from a gaseous suspension of particles which enables the separation of particles with high resolution.

It is a still further object of the invention to provide improved apparatus for the separation of gas borne particles through the use of collimated beams of such particles so that the particles of selected size may be monitored and analyzed for composition.

Briefly described, particle separating aparatus involving the invention may be used for the separation of gas suspended particles, including molecules, and comprises means for generating by expansion of the suspending gas, a continuum source particle beam. To this end a nozzle introduces the particles at substantially the same radial position spaced from the axis of the nozzle into a vacuum environment. The nozzle may have flows of gas delivered to it, with a clean flow of particle free gas at the core and another clean flow of particle free gas sheathing the particle containing gas. The trajectories of the particles in the beam are thereby precisely defined. Means spaced from the nozzle exit along the nozzle axis where the trajectories become straight lines are operative to separate by transmission or collection only those particles having the selected trajectory. These particles have the same parameters characterized by the vlaue of the dimensionless quantity, $\beta$, defined hereinafter. The separating means may be a collimator having a hole of such dimensions and located with respect to the nozzle exit so as to characterize the parameters (mass and dimensions) of the particles to be separated. A plurality of collimators, each of which define different trajectories, provide a double valued transmission characteristic for each collimater except for a collimating hole located on the beam axis which provides only one transmission peak. Such collimators may be combined to provide collection peaks extremely sharp in slope and narrow that enable molecules which are close to each other in molecular weight to be separated.

Other features, objects and advantages of the invention will become more apparent from the reading of the following description in connection with the accompanying drawings in which.

Although these drawings refer only to preferred embodiments corresponding to the collimating hole or holes all being centered on the beam axis, it is to be understood that one or more collimating holes can also be located at various off-axis positions. The transmission efficiency of the off-axis collimators will not be single valued, as in the on-axis arrangement for a single collimator, and may not be as suitable as the on-axis arrangement for some applications.

Figure 1:
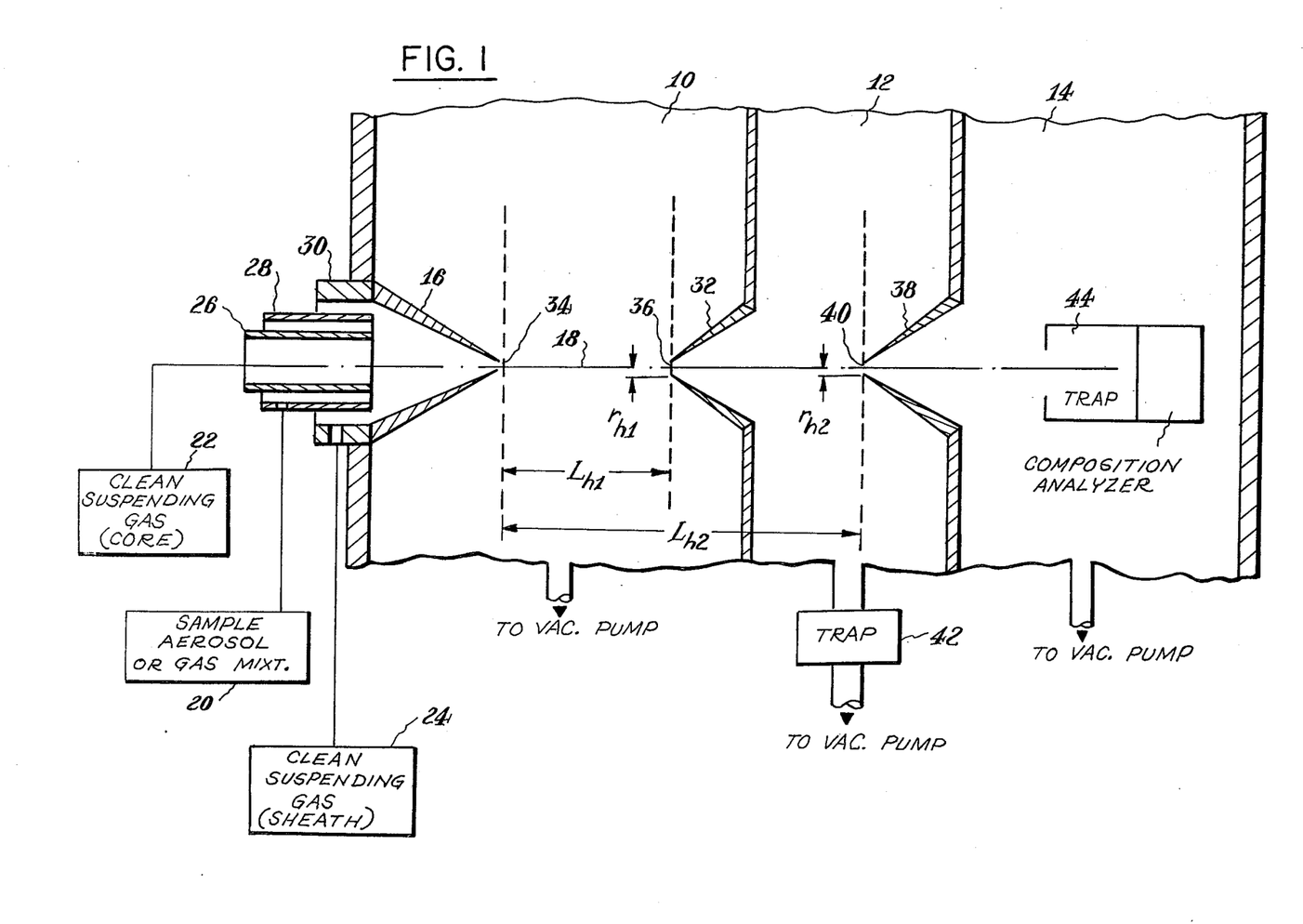
FIG. 1 is a schematic diagram of apparatus for the separation of gas borne particles in accordance with the invention.
Figure 6:
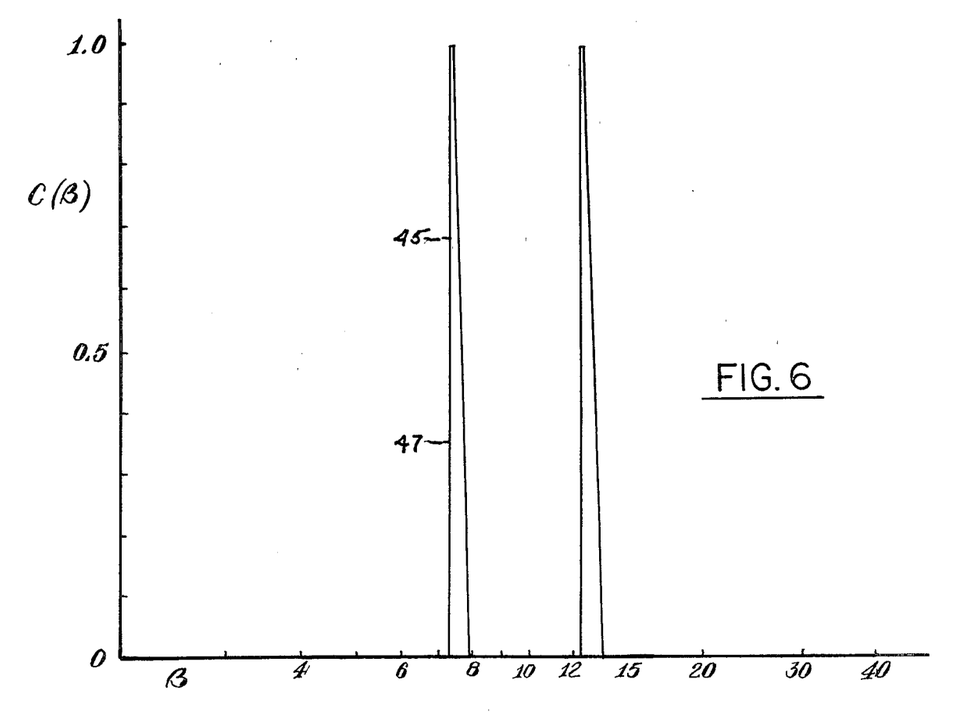
FIG. 6 is a plot illustrating the high resolution obtainable through the use of a pair of collimators in terms of the collection efficiency, C $(\beta)$ vs. $\beta$ for exemplary values of flow, $Q_c/Q_o = 0.70$, $Q_s/Q_o = 0.20$, trajectory angle of the first collimator hole, $\theta_{h1} = 1.20°$ and second trajectory angle for the second collimator $\theta_{h2} = 1.00$ degrees, ratio of specific heats $= 1.40$, and total nozzle included angle $2\phi = 30°$.

Referring more particularly to the drawings, there is shown in FIG. 1 a vacuum environment containing three vacuum chambers 10, 12 and 14 each of which may be evacuated to high vacuum, suitably $10^{-4}$ Torr. Vacuum pumps connected to the chambers, such as diffusion pumps, provide the high vacuum. A nozzle 16 which converges at the total included angle $2\phi$ to the axis 18 thereof generates a continuum source particle beam from particles in a gas suspension, such as a sample aerosol or gas mixture cont double valued collection efficiency, C ($\beta$), for such a system of the two collimators 32 and 38. This function is illustrated in FIG. 6 and will be discussed more fully below. The sharp, highly sloped characteristic due to the clean gas core flow and to the co-axial collimation enables separation of particles, such as gas molecules which are close in molecular weight. FIG. 6 shows two points 45 and 47 where the collection efficiency of one species of particle is considerably different than for another (i.e. the particles whose value is approximately 7.5 at point 45 has a collection efficiency of about 67% while the collection efficiency of particles whose $\beta$ value is approximately 7.2 is only 38%). The collection efficiency of the heavier molecule will then be twice that of the lighter molecule whose value is smaller. The relative quantity of heavier molecules collected in the trap 42 (i.e. the relative concentration of such heavier molecules) is thereby increased by reason of the apparatus.

Figure 2:
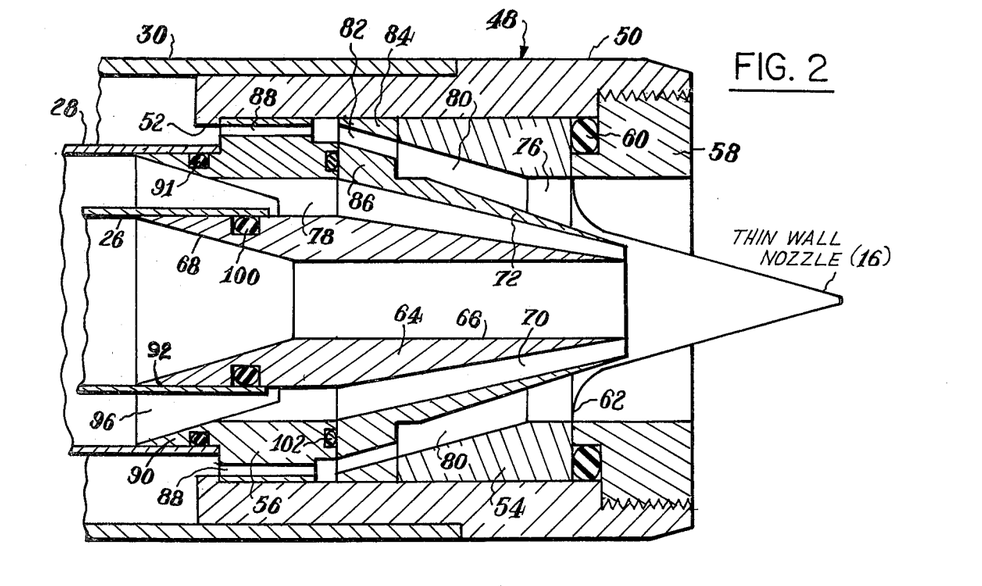
FIG. 2 is a diametral sectional view of the nozzle and the means for introducing flows of gas to form a continuum source particle beam which is used in the apparatus shown in FIG. 1.

A presently preferred form of the nozzle assembly is shown in FIG. 2. The nozzle itself may be a thin walled structure consisting of a sheet of stainless steel. The nozzle 16 is arranged in a cylindrical mount assembly 48 having an exterior cylinder 50 with a lip 52. The lip 52 holds a cyliner 54 and another cylindrical member 56. The outer edge of the member 56 engages a step formed by the lip 52. A threaded disc 58, which encases an "O" ring 60, clamps the flared inlet end 62 of the nozzle 16 against the forward end of the cylinder 54.

The cylindrical member 56 has a central section 64 having a bore 66 with a tapered section 68 at its rear end. A cylindrical channel 70 is formed between the cylinder 54 and member 56 by a tapered wall 72 thereof. This channel 70 communicates with holes 78 in the cylindrical member 56 to provide an axially symmetric channel for the particle containing flow. The core flow is provided through the bore 66. The outer sheath clean gas flow is provided by a bore 80 in the cylinder 54, and holes 82 through the rear portion (84, 86) of cylinder 54. These holes 82 connect to a series of holes 88 in the member 56. The passage consisting of the bore 76, bore 80, holes 82 and holes 88 carry the outer sheath flow of clean gas. Concentric tubes 26, 28 and 30 slide over the outer cylinder 50, the exterior end 90, and the interior wall 92 of a tapered bore 96 in the cylindrical member 56. "O" rings 98, 100 and 102 prevent leakage between the flows.

Couplings connect cylinders which provide the sources of the gas to the tubes 26, 28 and 30. These couplings, the gas containing cylinders and the pressure regulating flow restrictions are not shown to simplify the illustration.

The following theoretical presentation illustrates the operation of the apparatus in separating the particles which are suspended in the gas supplied to the nozzle 16. In order to determine the trajectory of a particle in the beam, the gas flow field and state properties are first calculated for the subsonic flow in the converging nozzle 16, the transonic flow in the exit region of the nozzle, and the supersonic free-jet flow up to the skimmer 32 which may be located a distance of 50, 100 or more diameters of the nozzle exit 34 from the nozzle exit plane. Consider that the flow is an isentropic-continuum expansion. The transition from continuum to free-molecule expansion is ignored, since the suspended particles have already obtained their final straight-line trajectories when this transition occurs.

The particle trajectories in the expanding gas flow are determined considering the presence of a particle does not distort the flow field. Thus the particle equation of motion, $$m_p \frac{dV_p}{dt} = -f(V_p - V_g), \quad (1)$$

where $m_p$ is the particle mass, $\vec{V}_p$ and $\vec{V}_g$ are the local particle and gas velocity vectors, t is the time, and f is the particle friction coefficient, can numerically be solved to determine the trajectory of a particle. In order to obtain such a numerical integration, an initial particle location and velocity is considered. When the initial particle location is sufficiently far upstream from the plane of the nozzle exit 34 (e.g., 50 or 100 nozzle diameters or more), the trajectory beyond the first few nozzle diameters is insensitive to the initial velocity of the particle. Thus, the particles can be taken to have equal particle and gas velocity at the plane of the nozzle inlet.

The equation of motion is non-dimensionalized by multiplying through $D^*/\bar{c}_o^2$, where $D^*$ is the nozzle flow diameter and $\bar{c}_o$ is the mean thermal speed of the suspending gas molecules in their stagnation state (the stagnation condition is indicated in the equations and elsewhere herein by the subscript o) giving the dimensionless form $$\frac{dU_p}{d\tau} = -\frac{fD^*}{m_p\bar{c}_o}(U_p - U_f), \quad (2)$$

where $\vec{U}_p = \vec{V}_p/\bar{c}_o$, $\vec{U}_f = \vec{V}_f/\bar{c}_o$ and $\tau = \bar{c}_o t/D^*$. The mathematical form of this equation requires that particles having the same value of the dimensionless group $\alpha = fD^*/(m_p\bar{c}_o)$ and having the same initial location in the converging nozzle must obtain the same trajectory.

For small solid particles or liquid droplets in a continuum-isentropic expansion, such that the particle is sub-micron in diameter but much larger than molecular sizes, the dimensionless group $\alpha$ obtains the form $$\alpha = 9\sigma\mu D^*/(\rho_p D_p \bar{c}_o C\lambda), \quad (3)$$

where $\sigma$ and C are constant shape factors and $\mu$ and $\lambda$ are the local gas viscosity and mean-free-path length, $\rho_p$ is the particle mass density and $D_p$ is the equivalent-volume-sphere diameter of the particle. All quantities in equation (3) are constant throughout the particle motion except for the ratio $\mu/\lambda$ which, for a continuum-isentropic flow, can be represented in terms of the local Mach number M according to $$\mu/\lambda = 0.499 \, \rho \, \bar{c} = 0.499 \, \rho_o \bar{c}_o [1 + (\gamma - 1)M^2/2]^{-\frac{\gamma+1}{2\gamma-2}},$$

where $\rho$ is the local gas density, $\bar{c}$ is the local mean thermal speed of the gas molecules and $\gamma$ is the ratio of specific heats for the gas. Thus, $$\alpha = (4.491/\beta)[1 + (\gamma - 1)M^2/2]^{-\frac{\gamma+1}{2\gamma-2}}, \quad (5)$$

where $\beta$ is called the dimensionless particle size, $$\beta = D_p\rho_p C/(D^*\rho_o\sigma). \quad (6)$$

particles having the same value of $\beta$ and the same initial location must obtain identical trajectories; i.e. the particle trajectory in the gas flow is completely controlled by the value of $\beta$ and the initial location of the particle at the inlet of the nozzle (the nozzle entrance plane).

Accordingly, where all of the particles are introduced at the same initial location and where the collimator, such as the skimmer 32, is properly positioned, only those particles obtaining the trajectory corresponding to a certain $\beta$ value are transmitted through the hole 36. With the axially symmetric flow shown in FIG. 1 of the drawings, the particles are introduced at the nozzle entrance plane at the fixed radius, i.e., over an annular cross-section centered on the nozzle axis 18. The annular flow of suspended particles contained between the core flow of clean gas of circular cross-section on the inside and the sheath flow of clean gas of annular cross-section on the outside, both of these flows being centered on the nozzle axis 18, fix the entrance location of the particles. A particle's trajectory therefore depends only on the particles $\beta$ value.

For the simple, axially symmetric system, the preferred skimmer location is centered on the jet axis. In this system only particles having a centain $\beta$ value will be transmitted through the collimator 32. Thus, particles of a desired size can be isolated by controlling their value of $D^*$ and/or $\rho_o$, so that only the desired size $= D_p \rho_p$ is transmitted, the transmitted value of $\beta$ being fixed.

A similar mathematical description and the identical physical description applies to beams of heavy "seed" molecules in a jet of lighter suspending gas molecules, i.e., to seeded molecular beams. By use of the low velocity asymptotic form of the friction factor derived by Schwartz and Andres, J. Aero. Sci., 7, 281 (1976), the result for the dimensionless group $\alpha$ is $$\alpha = (3.505/\beta)[1 + (\gamma - 1)M^2/2]^{-\frac{\gamma+5}{6\gamma-6}}, \quad (7)$$

where $\beta$ is now the dimensionless particle mass, $$\beta = (\nu^2 + \nu)^{1/2}(kT_o)^{4/3}/(C_6^{1/3}D^*p_o) \quad (8)$$

with $\nu = m_p/m_g$, $m_p$ and $m_g$ the particle (seed molecule) and suspending gas molecule masses, k the Boltzmann's constant, $T_o$ and $p_o$ the stagnation temperature and pressure of the suspending gas, and $C_6$ the London interaction coefficient: the constant of proportionality between the attractive interaction energy for a seed and suspending gas molecule pair and the inverse sixth power of their separation. The constant $C_6$ can be regarded as a measure of molecular size. Thus, the collimation spearation apparatus can be used to separate molecular species in a gas mixture according to mass and the value of $C_6$ (size) as well as suspended solid particles and droplets according to mass and size. Other definitions of $\beta$ apply for other cases such as for particles larger than single molecules but smaller than a few hundredths micron diameter and for particles of about one micron diameter and larger.

Upon penetrating into the vacuum chamber a distance of several nozzle diameters beyond the nozzle exit, the beam particles have obtained their final (terminal) trajectory. That is, the suspending gas has become so dilute it no longer exerts significant influence on the particle motion and the beam particles continue on straight line trajectories already established at this location. Let $\theta$ denote the angle between this terminal particle trajectory and the beam axis. Then $$\tan\theta = V_r/V_x \quad (9)$$

where $V_r$ and $V_x$ are the terminal velocity components of the particle in the radial and axial directions. Moreover, to adequate approximation at sufficiently large x, $$r = x \tan\theta \quad (10)$$

Figure 3:
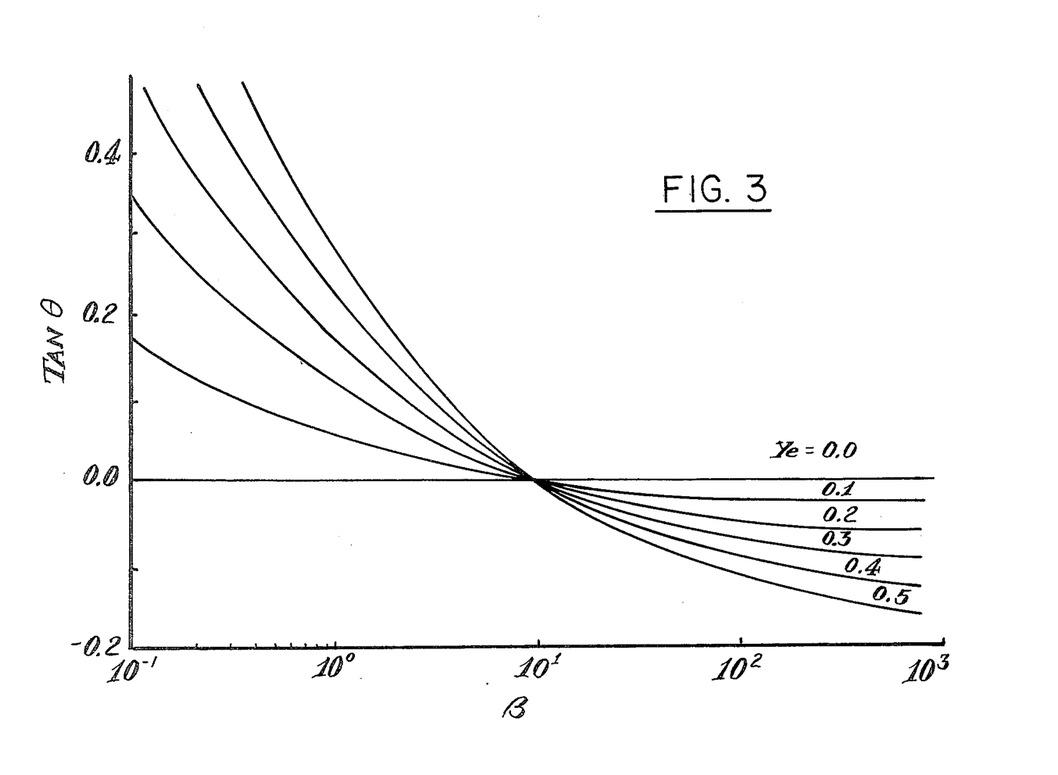
FIG. 3 is a curve illustrating the inclination of the particle trajectories to the axis of the particle beam for various dimensionless locations at the nozzle exit, $y_e$.

FIG. 3 shows the somewhat idealized results of many calculations of $\tan\theta$ for $\gamma = 1.4$ and for a conical converging nozzle of 30° total included angle. The parameter $y_e = r_e/D^*$ is the dimensionless radial position in the nozzle exit plane. Negative values of $\tan\theta$ indicate the particle has crossed the beam axis. Thus, the large particles (because of their large inertia) retain some of their inward radial velocity component obtained in the converging nozzle section, cross the beam axis and form a diffuse (wide angle) beam.

At the opposite extreme, small particles (because of their low inertia) lose all their inward radial velocity component before nearing the beam axis and, in fact, obtain an outward radial velocity component from the radial expansion of the suspending gas before it has become too dilute to influence particle motion. Particles of small $\beta$ thus also form a diffuse beam.

At just the right intermediate value of $\beta$, 9.70 for the present example, the beam particles just lose their radial velocity component upon reaching the beam axis. A beam of these particles is not diffuse but highly concentrated. If such a beam is directed at a small collimating hole of radius $r_h$ and separation from the nozzle exit $L_h$ such that $$\tan\theta_h = r_R/L_R \quad (11)$$

particles for which $\beta = 9.70$ will be transmitted through the hole with approximately 100 percent efficiency while particles increasingly larger and smaller will be transmitted with increasingly poorer efficiency.

Figure 4:
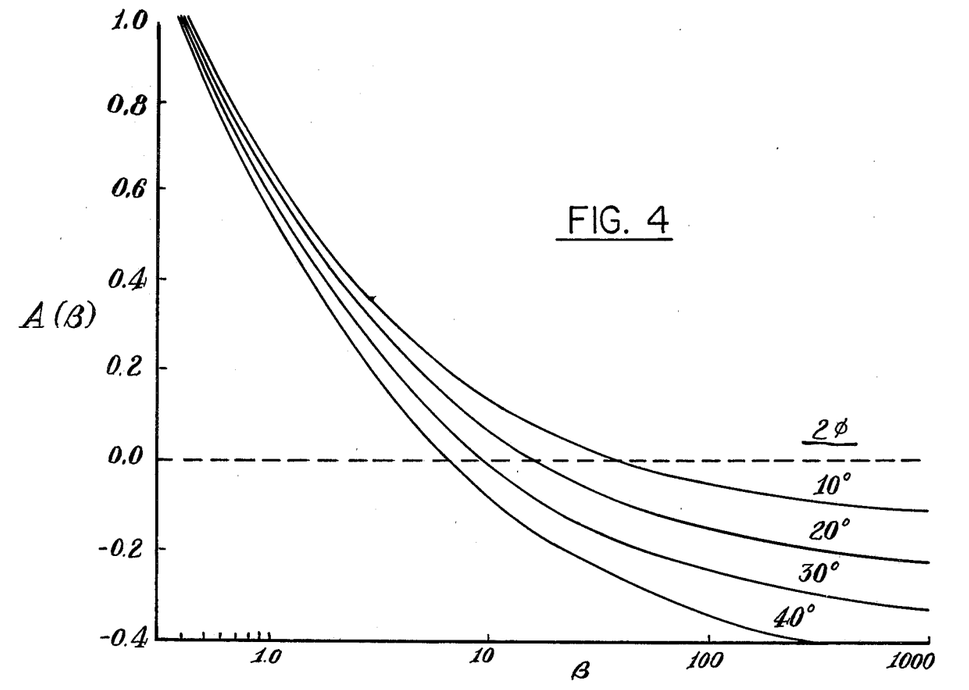
FIG. 4 is a graph illustrating the trajectory function A $(\beta)$ vs. $\beta$ for conical converging nozzles of various total included angle $2\phi$

Numerous numerical trajectory calculations indicate that, to adequate first approximation, the terminal particle trajectories are described by $$\tan\theta = y_e A(\beta) \quad (12)$$

where the function $A(\beta)$ in FIG. 4, has been extracted from data like that of FIG. 3. Expressions (11) and (12) can be combined to define the condition for particle transmission through the collimating hole, namely, $$\tan\theta < \tan\theta_h \text{ or } y_e < \frac{r_h}{L_h A(\beta)} \quad (13)$$

this limiting condition (upper limit of integration over $y_e$), together with the assumptions of uniform gas flow and particle concentration across the nozzle exit plane, gives the particle transmission efficiency through the collimating hole $$T(\beta) = \frac{4\tan^2\theta_h}{A^2(B)} \text{ or } 1.0 \quad (14)$$

whichever is less.

Figure 5A:
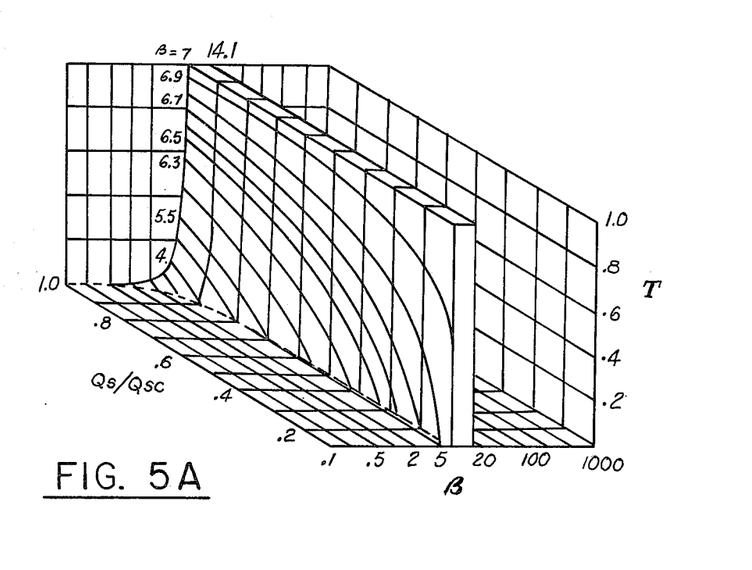
FIGS. 5A and 5B illustrate the transmission efficiency characteristic, T $(\beta)$ vs. the dimensionless particle quantity, $\beta$, for various particle containing flows $Q_s$ which are located between a central core flow $Q_c$ and an outer sheath flow $Q_o\text{-}Q_s\text{-}Q_c = Q_o\text{-}Q_{sc}$ which make up a total nozzle flow $Q_o$ for the exemplary case where $Q_{sc}$ is equal 0.36 $Q_o$.
Figure 5B:
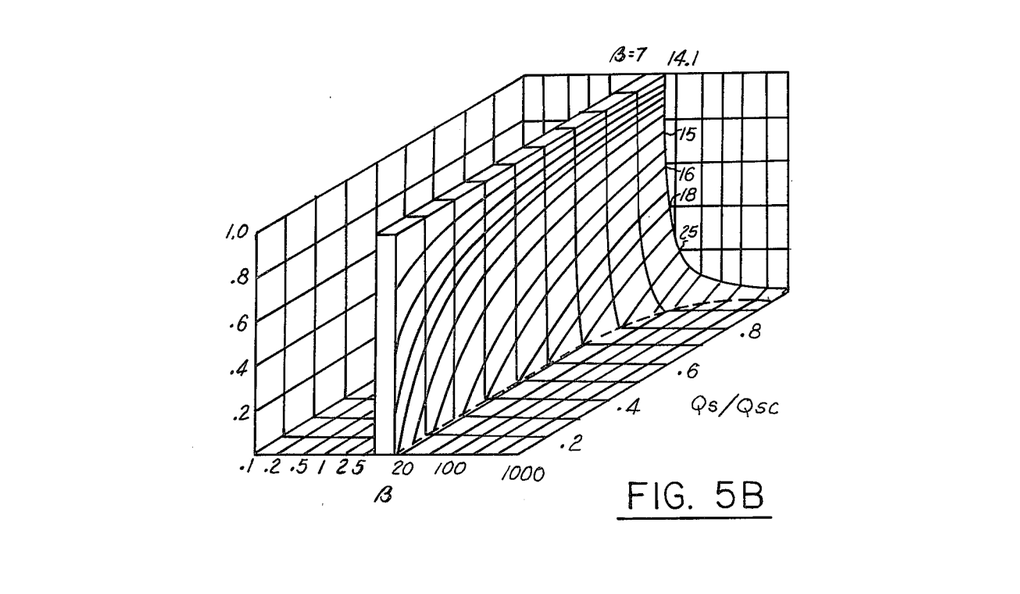

Because particles of any $\beta$ will penetrate the collimating hole if they are sufficiently near the nozzle exit, the transmission function (14) has long "tails" at high and low $\beta$ values. As illustrated in FIG. 5, these tails are removed, sharply enhancing the resolving power of the collimation separator, by introducing the core flow $Q_c$ of particle free suspending gas. To further enhance resolving power, complications due to boundary layer effects are also reduced or removed by introducing the outer sheath flow of particle free suspending gas such that the sample flow $Q_s$ is contained in an annular cross-section surrounded by the core flow $Q_c$ on the inside and the sheath flow $Q_o - Q_s - Q_c$ on the outside, where $Q_o$ is the total flow through the nozzle. Performing the integration with the same considerations as before, but now incorporating the proper lower and upper limits of integration, the transmission efficiency function becomes $$T(\beta) = \frac{4\tan^2\theta_h/A^2(\beta) - Q_c/Q_o}{Q_s/Q_o} \quad (15)$$

subject to the restriction $O \leqq T(\beta) \leqq 1.0$. This function is illustrated in FIG. 5 for the case when $\theta_h = 1.0°$ and $Q_{sc} = Q_s + Q_c = 0.36\ Q_o$. Of course, in the special case when $Q_s = Q_o$, equation (15) is reduced to equation (14). Thus, the transmission function of equation (14) is similar (but not identical) to the case $Q_s/Q_{sc} = 1.0$ in FIG. 5 (because of the denominator $Q_s/Q_o$ in equation (15) which does not occur in the simpler expression, (14)).

Although the peak of the transmission function occurs at a fixed value of $\beta$, the collimation separation process is readily used to isolate particles or molecules of selected size or weight. As indicated by equation (6), this is accomplished by adjusting $\rho_o$ (source density of the suspending gas) or D* (nozzle flow diameter) so that $\beta$ obtains the proper value for the selected particle size.

Size resolution is enhanced by placing two collimating holes, (36, 40) in collimating skimmers 32 and 38 in series. The collection efficiency $C(\beta)$ for the capture of beam particles in the chamber 12 between the inlet and outlet collimating holes 36 and 40 will be given by the difference between the two appropriate transmission efficiency functions (15). That is, $$C(\beta) = T(\beta)_{36} - T(\beta)_{40} \quad (16)$$

The form of $C(\beta)$ is illustrated in FIG. 6. Two transmission peaks are always present for such a system. However, the $\beta$ location of both peaks can be selected so that interference effects are minimized.

The curves of FIG. 3 and the preliminary measurements described by Dahneke and Hoover (hereinbefore cited) indicate that a collection system operating at small $\beta$ values, such that the relatively steep portions of the curves of FIG. 3 apply, will provide the best resolution in separating particles of nearly the same $\beta$, such as uranium hexafluoride isotopes. Refer to the curves of FIG. 3. Particles introduced at a given dimensionless radius at the nozzle inlet plane $y_i$, where $y_i y_e$ in the simple one-dimensional model calculations used to obtain the data of FIG. 3, will obtain the largest changes in tan $\theta$ for a fixed change in $\beta$ in the small $\beta$ range.

In addition, from the above equations (10) and (12), $$\left(\frac{\partial \tan\theta}{\partial\beta}\right)_{yi} = \frac{1}{x}\left(\frac{\partial r}{\partial\beta}\right)_{yi,x} = y_i\frac{dA(\beta)}{d\beta} \quad (17)$$

that is, the resolving power, R, is defined by $$R = \left(\frac{\partial r}{\partial\beta}\right)_{yi,x} = xy_i\frac{dA(\beta)}{d\beta}. \quad (18)$$

This expression together with the curves of FIG. 4 also indicates the best $\beta$ resolution in $C(\beta)$ (best resolving power) will be obtained by use of two co-axial skimmers 32 and 38 located at large x, with $\beta$ small ($\beta < 9.70$), $y_i$ near its maximum of approximately 0.5, and $2\phi$large so that $dA(\beta)/d\beta$ will have large (negative) magnitude. Under these conditions $|R|$ is large so that a particle species can be most efficientyl isolated in the chamber 12 from another species having nearly the same $\beta$ value which will be isolated in the chamber 14. The $y_e$ dependence of $r = x \tan\theta$, however, becomes strong at the same small $\beta$ values. That is, to realize the benefit of large resolution at small $\beta$, the suspended particles must be contained within a very narrow range of $y_e$.

Moreover, although the simple model calculations have ignored boundary layer effects, such effects can be utilized to greatly enhance the resolving power R $= (\delta r/\delta\beta)_{yix}$. Such effects will enhance resolving power because they will operate to decrease $V_x$ and to increase $V_r$, such that $\tan\theta = V_r/V_x = r/x$ will be substantially increased, with a corresponding increase in resolving power.

Efficient operation of a system using boundary layer effects to enhance resolving power will require confinement of the suspended particles to a very narrow range of $y_e$ within the boundary layer. Such confinement can be effectively accomplished by various methods such as by mechanically separated flows merging near the nozzle exit plane or by boundary layer injection of the suspended particle flow through the nozzle wall near the nozzle exit plan followed, just downstream, by boundary layer injection of a clean gas sheath flow.

I claim:

1. Apparatus for separation of gas borne particles of selected dimensions and mass having a nozzle which delivers a particle suspension into a vacuum environment forming a continuum source particle beam, the improvement which comprises means for delivering into said nozzle separate flows of gas respectively containing said particles and free of said particles with said particle free flow being along the axis of said nozzle and said particle containing flow being spaced outward from the center of said axis, and separator means with at least one collimator having an aperture aligned with said nozzle, said delivery means including first means for introducing into said nozzle a core flow of said particle-free gas, second means for introducing into said nozzle said particle containing gas surrounding said core flow and third means for introducing into said nozzle a sheath flow of said particle free gas between said flow of particle containing gas and the wall of said nozzle.

2. The invention as set forth in claim 1 wherein a plurality of concentric tubes is connected to said nozzle and is coaxial with said nozzle, and means for connecting a source of said particle free gas to the center one of said tubes and a source of particle containing gas to at least one of said plurality of tubes other than said center tube.

3. The invention as set forth in claim 1 wherein said nozzle has an inlet, three concentric tubes connected to said nozzle inlet and coaxial therewith, the inner of said three tubes defining a first channel, the intermediate and inner of said three tubes defining a second channel, the outer said tubes and the intermediate of said three tubes defining a third channel, means connecting a source of said particle free gas to said first and third channels and a source of said particle containing gas to said second channel.

4. The invention as set forth in claim 1 further comprising means included in each of said first, second and third introducing means for varying the pressures of the gases introduced into said nozzle whereby to vary the stagnation density of the gases from which said beam is generated for varying the trajectories of the particles in said beam so as to enable particles of selected size and mass to be separated.

5. The invention as set forth in claim 1 wherein said separating means comprises a plurality of coolimators each spaced from each other a line extending away from said nozzle exit and having holes intersected by said line of dimensions such that the tangents of the angles defined by the ratio of the radial distances from the intersections of said line and the plane of said holes to the distances from the plane of said holes to the nozzle exit are different.

6. The invention as set forth in claim 12 wherein said separating means comprises at least one collimator having a hole.

7. The invention as set forth in claim 1 wherein said separating means comprises a plurality of collimators each disposed to pass particles characterized by a different value of $\beta$ as defined in equation (6) or (8) of the specification.

8. The invention as set forth in claim 1 further comprising means spaced away from the exit of said nozzle along the axis thereof a distance, $L_h$, equal or longer than the distance which is sufficient for the gas in which said particles are suspended to become so dilute that it no longer has a significant influence on the motion of the particles and defining a collimating hole of size $r_h$ measured perpendicular to said axis such that $r_h/L_h$ equals the tangent of an angle $\theta_h$ within which the particles of the selected size and mass travel from said nozzle exit, and said means for delivering said separate flows into said nozzle are operative to introduce said particles at said nozzle exit at substantially the same initial locations on their trajectories.

9. The invention as set forth in claim 8 further comprising means defining a second collimating hole disposed a distance $L_{h2}$ longer than than $L_h$ away from said nozzle exit along said nozzle axis, said hole being of a size $r_{h2}$ measured perpendicular to the nozzle axis such that $r_{h2}/L_{h2}$ equals the tangent of an angle $\theta_{h2}$ which is different from tangent $\theta_h$ to separate particles which are in different groups of size and mass each containing particles the trajectories of which travel through said first named collimating hole but do not travel through said second collimating hole.

10. The invention as set forth in claim 1 wherein means are provided for collecting said separated particles.

11. The invention as set forth in claim 10 further comprising means for analyzing the composition of said collected particles.

12. The invention as set forth in claim 1 wherein said separating means include means disposed along trajectories of particles having parameters characterized by approximately the same value of the dimensionless quantity $\beta$ as defined by equation (6) or (8) of the specification.

13. The invention as set forth in claim 12 wherein said separating means is operative to separate particles of different species having nearly the same value of $\beta$ comprising first and second vacuum chambers, a pair of collimators co-axial with each other and disposed successively down-stream of said nozzle exit, said first chamber being disposed between said first and second collimators, and means for collecting said first species in said first chamber and said second species in said second chamber.

* * * * *